(12) United States Patent
Ford et al.

(10) Patent No.: US 8,740,261 B2
(45) Date of Patent: Jun. 3, 2014

(54) FITTING ASSEMBLY

(75) Inventors: Douglas W. Ford, Wilsonville, OR (US); Robert DeLine, Corbett, OR (US)

(73) Assignee: Optimize Technologies, Inc., Oregon City, OR (US)

( * ) Notice: Subject to any disclaimer, the term of this patent is extended or adjusted under 35 U.S.C. 154(b) by 0 days.

(21) Appl. No.: 13/475,852

(22) Filed: May 18, 2012

(65) Prior Publication Data
US 2012/0319400 A1   Dec. 20, 2012

Related U.S. Application Data

(63) Continuation-in-part of application No. 12/476,931, filed on Jun. 2, 2009, now Pat. No. 8,201,854.

(60) Provisional application No. 61/058,091, filed on Jun. 2, 2008.

(51) Int. Cl.
*F16L 25/00*   (2006.01)

(52) U.S. Cl.
USPC ............................ 285/385; 285/342; 285/353

(58) Field of Classification Search
USPC ................. 285/385, 353, 339, 341, 342, 343
See application file for complete search history.

(56) References Cited

U.S. PATENT DOCUMENTS

| | | | |
|---|---|---|---|
| 2,663,753 A | 12/1953 | Bird | |
| 3,332,708 A | 7/1967 | Jackson | |
| 3,893,716 A | 7/1975 | Moreiras | |
| 4,205,417 A | 6/1980 | Mackal | |
| 4,281,679 A * | 8/1981 | Stearns | 137/515.5 |
| 5,375,887 A | 12/1994 | Johnson | |
| 5,472,598 A | 12/1995 | Schick | |
| 5,525,303 A | 6/1996 | Ford | |
| 5,669,637 A | 9/1997 | Chitty | |
| 6,095,572 A | 8/2000 | Ford | |
| 6,494,500 B1 | 12/2002 | Todosiev | |
| 7,014,222 B1 | 3/2006 | Poppe | |
| 7,316,777 B2 | 1/2008 | Loy, Jr. | |
| 7,641,242 B2 * | 1/2010 | Van Pelt | 285/384 |

(Continued)

FOREIGN PATENT DOCUMENTS

KR   10-2008-0049105 A   6/2008

OTHER PUBLICATIONS

Batts, IV, J.W., "All About Fittings," © 2003 John W. Batts, IV, Scivex, Upchurch Scientific Division, Oak Harbor, Wash., <http://web.archive.org/web/20061111132212/www.upchurch.com/PDF/Lit/fittingsbook.pdf>, [retrieved May 29, 2007], 63 pages.

(Continued)

*Primary Examiner* — Aaron Dunwoody
(74) *Attorney, Agent, or Firm* — Christensen O'Connor Johnson Kindness PLLC (57) ABSTRACT

A fitting assembly for use in a fluid transfer assembly includes a fluid conduit having a first fitting with first and second ends and a bore extending between the first and second ends for receiving the fluid conduit. The first end of the first fitting is configured to sealingly dispose a ferrule assembly within a second fitting in an engaged position. The fitting assembly further includes a third fitting having first and second ends and a bore extending between the first and second ends for receiving the fluid conduit. The first end of the third fitting is configured to sealingly dispose a collet assembly within the first fitting in an engaged position.

16 Claims, 8 Drawing Sheets

(56) References Cited

U.S. PATENT DOCUMENTS

| | | |
|---|---|---|
| 8,201,854 B2 | 6/2012 | Ford |
| 2008/0237112 A1 | 10/2008 | Ford |
| 2009/0295156 A1 | 12/2009 | Ford |
| 2010/0148501 A1 | 6/2010 | Bennett |
| 2010/0224543 A1 | 9/2010 | Ellis |
| 2010/0224546 A1 | 9/2010 | Ellis |
| 2011/0107823 A1 | 5/2011 | Dehmer |
| 2012/0014848 A1 | 1/2012 | Ellis |

OTHER PUBLICATIONS

Sonnenschein, A., and H. Knauer, "Dynaseal-Connection System for HPLC," Chromatographia 22(7-12):433, Dec. 1986.

"Valco Fittings," © 2003 VICI (Valco Instruments Co. Inc. and VICI AG), <http://web.archive.org/web/20061016005832/www.vici.com/vfit/ferrules.php>, [retrieved Sep. 29, 2009], 7 pages.

International Search Report and Written Opinion mailed Aug. 20, 2013, issued in corresponding International Application No. PCT/US2013/041901, filed May 20, 2013, 15 pages.

\* cited by examiner

FITTING ASSEMBLY

This application is a continuation-in-part of U.S. patent application Ser. No. 12/476,931, filed Jun. 2, 2009, which claims the benefit of U.S. Provisional Patent Application No. 61/058,091, filed Jun. 2, 2008, the disclosures of which are hereby incorporated by reference herein.

BACKGROUND

Numerous types of equipment used for the analysis or purification of chemical compounds utilize miniature fluid conduits, such as metallic tubing, through which liquid samples pass. An analytical technique, such as liquid chromatography, uses a column (conduit) packed with a packing material in order to analyze and identify chemical properties of certain fluids. For example, an analyte may be introduced into one end of the column, and a carrier fluid then run through the column. The length of time that the analyte is retained within the column can enable analysis and identification of the analyte. A popular form of liquid chromatography is High Performance Liquid Chromatography (HPLC) in which the sample is pumped through the column under an elevated pressure, typically at 300 to 6,000 psi. Another, relatively newer liquid chromatography form is Ultrahigh Pressure Liquid Chromatography (UHPLC) in which system pressure extends upward to 1400 bar or 20,000 psi, and possibly 30,000 psi. Both HPLC and UHPLC are examples of analytical instrumentation that utilize fluid transfer at elevated pressures.

Liquid chromatography systems, such as HPLC or UHPLC systems, typically include several components. For example, such a system may include a pump; an injection valve or autosampler for injecting the analyte; a precolumn filter to remove particulate matter in the analyte solution that might clog the column; a packed bed to retain irreversibly absorbed chemical material; the HPLC column itself; and a detector that analyzes the carrier fluid as it leaves the column. These various components may typically be connected by a miniature fluid conduit, such as metallic or polymeric tubing, usually having an internal diameter of 0.003 to 0.040 inch.

All of these various components and lengths of tubing are typically interconnected by threaded fittings. Fittings for connecting various components and lengths of tubing are disclosed in prior patents and patent applications, for example, U.S. Pat. Nos. 5,525,303; 5,730,943; 5,911,954; and 6,095,572; and U.S. Patent Application Publication No. 2008/0237112, filed on Jan. 9, 2008, the disclosures of which are herein all incorporated by reference.

Figure 1:
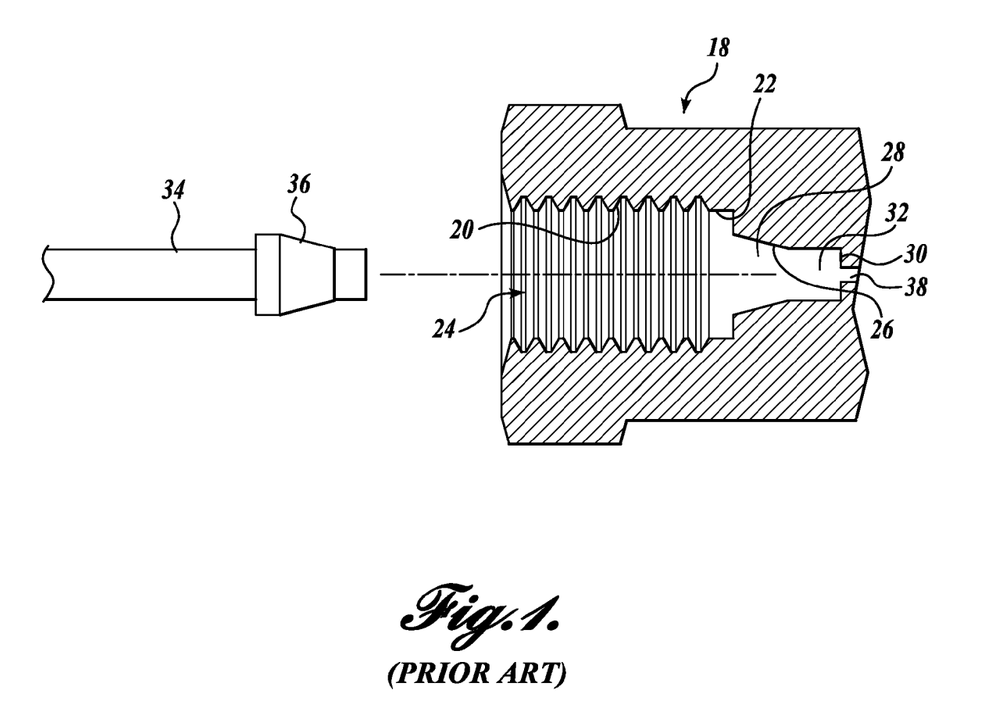
FIG. 1 is a partial cross-sectional view of a prior art fitting assembly for use in fluid transfer assemblies.

A typical threaded fitting 18 well known in the art is shown in FIG. 1. The threaded fitting 18 includes an internally threaded portion 20 formed near its open end that is suitable for threadably receiving a second fitting, tightening device, etc., having an external threaded portion (not shown). The fitting 18 further includes an internal passageway 24 that narrows in diameter at its distal terminus to form a female, cone-shaped chamber 28 defining a frusto-conical sealing surface 26. The cone-shaped chamber 28 is in communication with a cylindrical chamber 32 sized to receive tubing 34 therein. The cylindrical chamber 32 defines a "tube stop" 30 at its end that closely and fully receives the tip of the tubing 34.

Often, the tubing interfaces with the threaded fittings with a ferrule or similar sealing device (see ferrule 36 in FIG. 1). The ferrule includes a cone-shaped end that allows it to be compressed within the female cone-shaped chamber of the fitting and thus form a liquid-tight seal. As is well known in the art, the tubing must be seated on the bottom of the cylindrical chamber when the ferrule is received within the fitting in order to ensure good chromatography. This becomes even more critical in UHPLC where the negative effects are greater. If the tube is not bottomed out in the cylindrical chamber, the resulting chromatogram exhibits band broadening due to mixing of the sample with the mobile phase. The extra volume between the end of the tube and the cylindrical chamber bottom is known as "dead volume." It is preferred that all fitting connections after the pump be made as "zero-dead-volume" connections to keep band broadening to a minimum. Even in connections before the pump it can be critical that there is "zero-dead-volume" because the extra volume will change the exact nature of mixing solvents, giving a different delay volume from various fitting connections.

The ferrule also secures on the tubing to prevent the tubing from ejecting from the fitting at specified pressures. For instance, HPLC ferrules are typically rated for pressures up to 6,000 PSI, and UHPLC ferrules are typically rated for pressures up to 20,000 PSI. In UHPLC systems, stainless steel tubing is often used to accommodate the high pressures. The ferrules are also typically made of stainless steel to properly seal against the tubing and to prevent the tubing from ejecting at the high pressures. When the ferrule is forced into the female cone-shaped chamber of the fitting, the ferrule swages down onto the tubing to prevent the tubing from ejecting from the fitting. However, with the ferrule being made of stainless steel, the ferrule swages onto the stainless steel tubing as a hard swage. As such, the position of the stainless steel ferrule cannot be readjusted on the tube, if, for instance, it is desired to use the tubing with a different fitting or component. Thus, if the stainless steel ferrule/tubing is reused in a fitting of a slightly different size, a "dead volume" is likely created between the end of the tube and the cylindrical chamber tube stop, or the ferrule cannot seat in the female cone-shaped chamber of the fitting, thereby causing the connection to leak.

In HPLC systems, a ferrule made of a softer material may be used such that a hard swage does not result. For instance, a ferrule made from Polyetheretherketone (PEEK) or another similar material may be used to seal the tubing within the fitting. The PEEK ferrule creates a soft swage on the tubing; and therefore, the position of the PEEK ferrule can be adjusted for use within different fittings. However, PEEK ferrules cannot withstand the extreme pressures of UHPLC systems.

Thus, it is desired to have a ferrule that can be re-used in various UHPLC fittings while maintaining a liquid-tight seal and preventing the tubing from ejecting at high pressures.

In certain HPLC and UHPLC systems, it is sometimes desirable to use an inert capillary tube that may include polymeric material or fused silica. For instance, the tubing may be comprised of polymeric-clad fused silica or fused silica with polymeric sleeves at the ends of the tubing. To be used within UHPLC systems, however, the tubing must be able to withstand extreme pressures in excess of 5,000 psi, often approaching 20,000 psi and beyond. In that regard, the UHPLC systems require fitting ferrule assemblies to secure tubing in place while making and maintaining a leak-tight seal.

As noted above, traditional stainless steel ferrules work on stainless steel tubing in a single-use fashion by swaging or crimping onto the tube to grip and hold the tube in place within the fitting, while at the same time forming a seal at the connection. If stainless steel ferrules (or similar ferrules) are used with fused silica tubing, it is desirable to sleeve or clad the fused silica tubing with an outer layer of polymer, such as PEEK. The PEEK outer sleeve provides a cushion between the stainless steel ferrule and the fused silica tube to prevent fracturing of the fused silica.

A polymeric ferrule, such as a PEEK ferrule, creates a soft swage on the tubing. Therefore, a PEEK ferrule or similar ferrule does not fracture or deform the more delicate tubing, such as polymeric-clad fused silica or fused silica with polymeric sleeves at the ends of the tubing. Moreover, the tubing can be repositioned with respect to the PEEK ferrule, and the position of the PEEK ferrule can be adjusted for use within different fittings.

However, PEEK ferrules in use with these tubings cannot withstand the extreme pressures of UHPLC systems. Higher pressures are difficult to achieve with polymer ferrules due to the limited gripping ability of the ferrules on the outer polymer layer of the tubing. At high pressures, the capillary tube ejects, resulting in a system failure. In addition, the polymeric ferrule may creep on the tubing over time due to its limited gripping ability or due to elevated temperatures, thereby necessitating retightening within the fitting to reinstate the grip of the ferrule on the capillary tube.

A wrench or similar tool may be used to tighten the fitting assembly and further compress the ferrule within the fitting assembly and onto the tubing, thereby increasing the pressure capabilities of PEEK or similar ferrules. However, by using a wrench to tighten the fitting, as opposed to tightening the fitting by hand, the tubing is often forced too tightly into the fitting port. For instance, referring to FIG. 1, tubing 34 would be driven into the cylindrical chamber 32 and may abut up against the tube stop 30. If a more delicate material is used for the tubing, such as silica, the tubing may fracture due to the over tightening.

Thus, there is additionally a need for a fitting and/or ferrule assembly that grips and seals onto various types of tubes (such as stainless steel, polymer-clad fused silica, polymer-sleeved fused silica, etc.) used in HPLC and UHPLC systems without breaking or deforming the tube.

SUMMARY

A ferrule for use in a fluid transfer assembly having a fluid conduit is provided. The ferrule includes a frusto-conical seal portion having a tapered end and an enlarged end and a first cylindrical bore sized and configured to slidably receive a fluid conduit. The seal portion is formed from a first material suitable to seal the fluid conduit within a first fitting without substantially deforming the fluid conduit.

The ferrule further includes a frusto-conical collet portion having a tapered end and an enlarged end, wherein the enlarged end of the collet portion is mated with the enlarged end of the seal portion. The collet portion has a second cylindrical bore in substantial alignment with the first cylindrical bore and at least one axial finger extending along the tapered end that is configured to be biased into locking engagement with the fluid conduit. The collet portion is formed from a second material that substantially prevents deformation of the fluid conduit when the finger is biased into locking engagement with the fluid conduit.

A fitting assembly for use in a fluid transfer assembly includes a fluid conduit having a first fitting with first and second ends and a bore extending between the first and second ends for receiving the fluid conduit. The first end of the first fitting is configured to sealingly dispose a ferrule assembly within a second fitting in an engaged position. The fitting assembly further includes a third fitting having first and second ends and a bore extending between the first and second ends for receiving the fluid conduit. The first end of the third fitting is configured to sealingly dispose a collet assembly within the first fitting in an engaged position.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of the present disclosure will become more readily appreciated by reference to the following detailed description, when taken in conjunction with the accompanying drawings, wherein.

DETAILED DESCRIPTION

Figure 2:
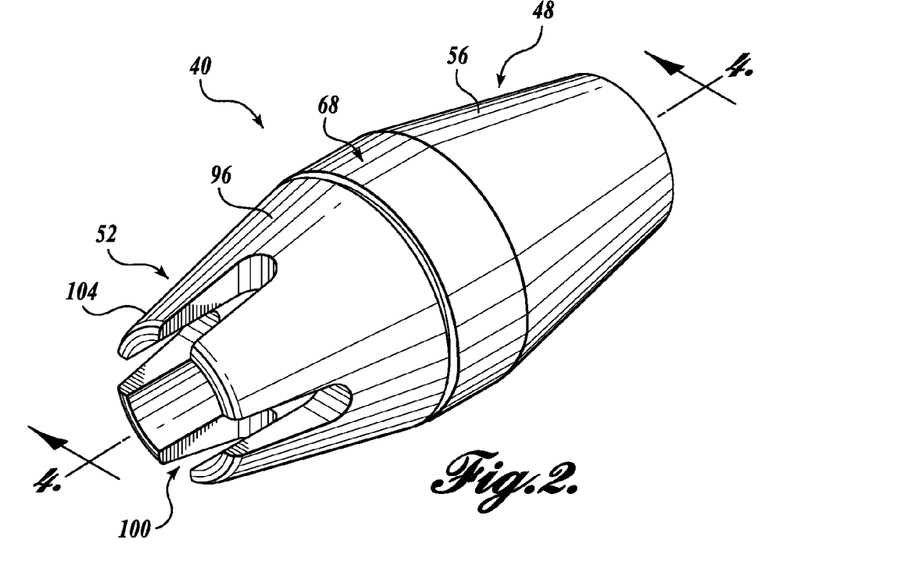
FIG. 2 is an isometric view of a hybrid ferrule formed in accordance with one embodiment of the present disclosure.
Figure 3:
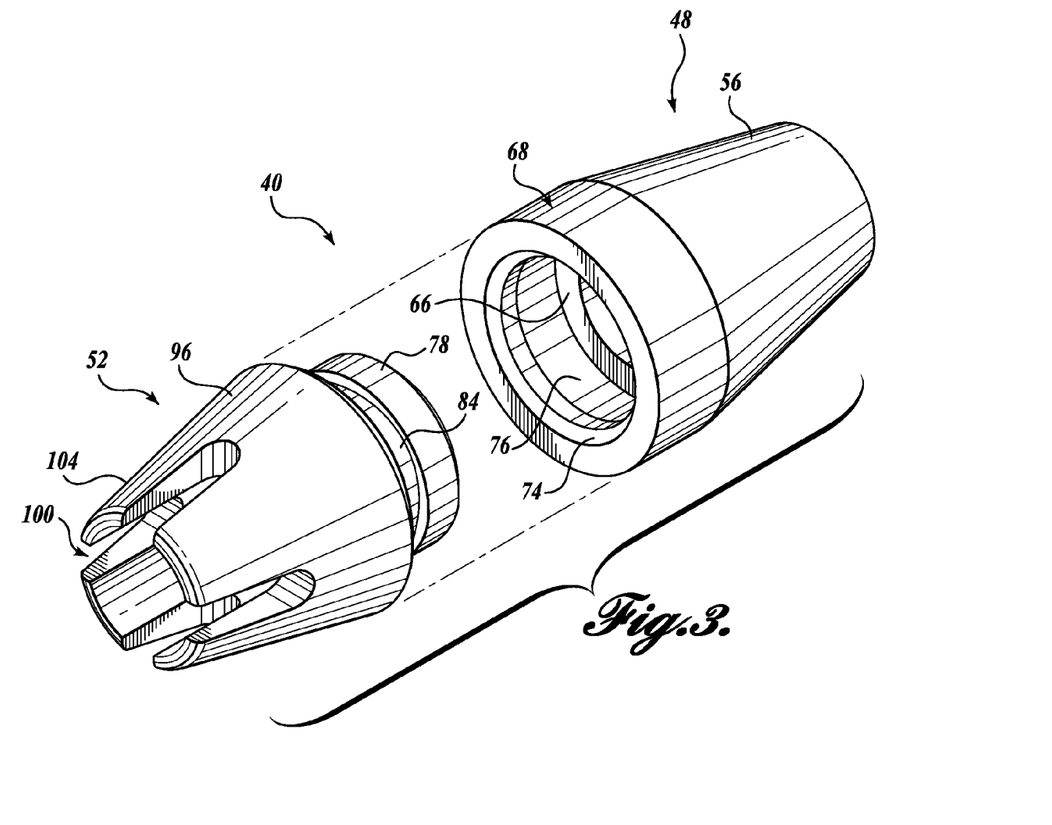
FIG. 3 is an exploded view of the hybrid ferrule of FIG. 2.
Figure 4:
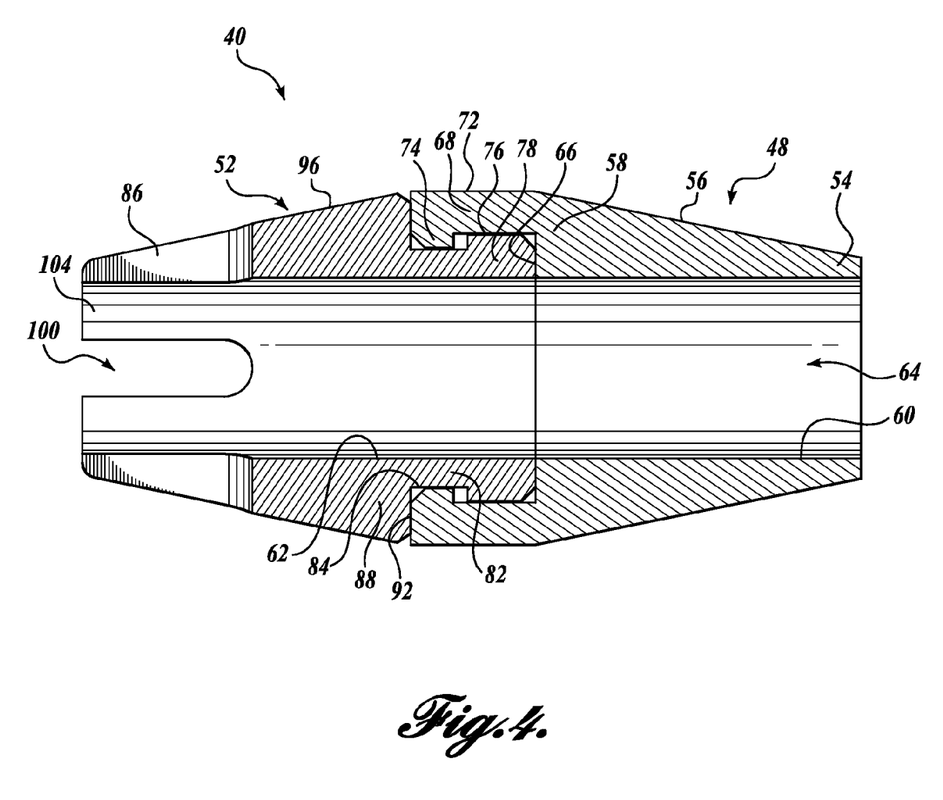
FIG. 4 is cross-sectional view of the hybrid ferrule of FIG. 2, taken substantially across line 4-4.

Referring to FIGS. 2-4, a hybrid ferrule 40 formed in accordance with one embodiment of the present disclosure is depicted. The hybrid ferrule 40 is suitable for use in fluid transfer assemblies for scientific instruments such as HPLC and UHPLC systems. For ease of description and illustration, the hybrid ferrule 40 will be hereinafter described as being used in a portion of a first exemplary embodiment of a UHPLC fitting assembly 44. However, it should be appreciated that the hybrid ferrule 40 may instead be used in any suitable system or assembly. Thus, the description hereinafter provided should not be seen as limiting the scope of the claimed subject matter.

Referring still to FIGS. 2-4, the hybrid ferrule 40 will now be described in detail. The hybrid ferrule 40 includes a seal portion 48 mated with a collet portion 52. The seal portion 48 is formed from a material suitable for sealing within the UHPLC fitting assembly 44, such as Polyetheretherketone (PEEK), and the collet portion 52 is formed from a material suitable for gripping onto the tubing of the fitting assembly 44, such as hardened Titanium alloy. The design and materials of the hybrid ferrule 40 allow the ferrule 40 to seal within a threaded fitting and withstand the extreme pressures of UHPLC, while at the same time being adjustable and reusable within various fittings, as will become apparent from the description below.

The seal portion 48 and collet portion 52 define first and second interior axial bore portions 60 and 62, respectively. The first and second interior axial bore portions 60 and 62 are substantially identical in diameter and cross-sectional shape such that when aligned, the first and second interior axial bore portions 60 and 62 define a substantially smooth interior cylindrical passageway 64 of constant diameter. In the alternative, the first and second interior axial bore portions 60 and 62 may instead define seal portion 48 and collet portion 52 interior surfaces that are textured, grooved, threaded, etc., to aid in gripping onto the exterior surface of the tubing 34. The interior cylindrical passageway 64 is configured to slidably receive a portion of a UHPLC fluid conduit therein. Preferably, the interior cylindrical passageway 64 receives stainless steel tubing 34 of a predetermined outer diameter having an internal fluid passageway 42. It should be appreciated that the first and second interior axial bore portions 60 and 62 may be any suitable size to define an interior cylindrical passageway 64 of a suitable diameter for receiving tubing of a desired size, material, etc., for different applications.

Both the seal portion 48 and the collet portion 52 are of a generally frusto-conical or cone shape to define a double-ended hybrid ferrule 40 when mated together. The seal portion 48 includes a tapered end 54 and an enlarged end 58, wherein the enlarged end 58 defines a transverse end surface 66. An exterior, substantially smooth tapered surface 56 extends from the enlarged end 58 to the tapered end 54 such that the seal portion 48 is suitably sized and shaped to be received within a portion of a threaded fitting. More specifically, the seal portion 48 is configured to be tightly received within the female, cone-shaped chamber 28 of the well known threaded fitting 18 described above with respect to FIG. 1 (the same threaded fitting 18 is shown in FIGS. 5A and 5B and will be described in further detail below).

Moreover, with the seal portion 48 being made from a suitable material such as PEEK, the seal portion seals against the fitting 18 and around the stainless steel tubing 34 to form a liquid-tight seal without deforming the stainless steel tubing 20. In this manner, the seal portion 48 forms a soft swage on the tubing 20 so that the hybrid ferrule 40 can be repositioned on the tubing 34 and reused in other fittings.

Figure 5A:
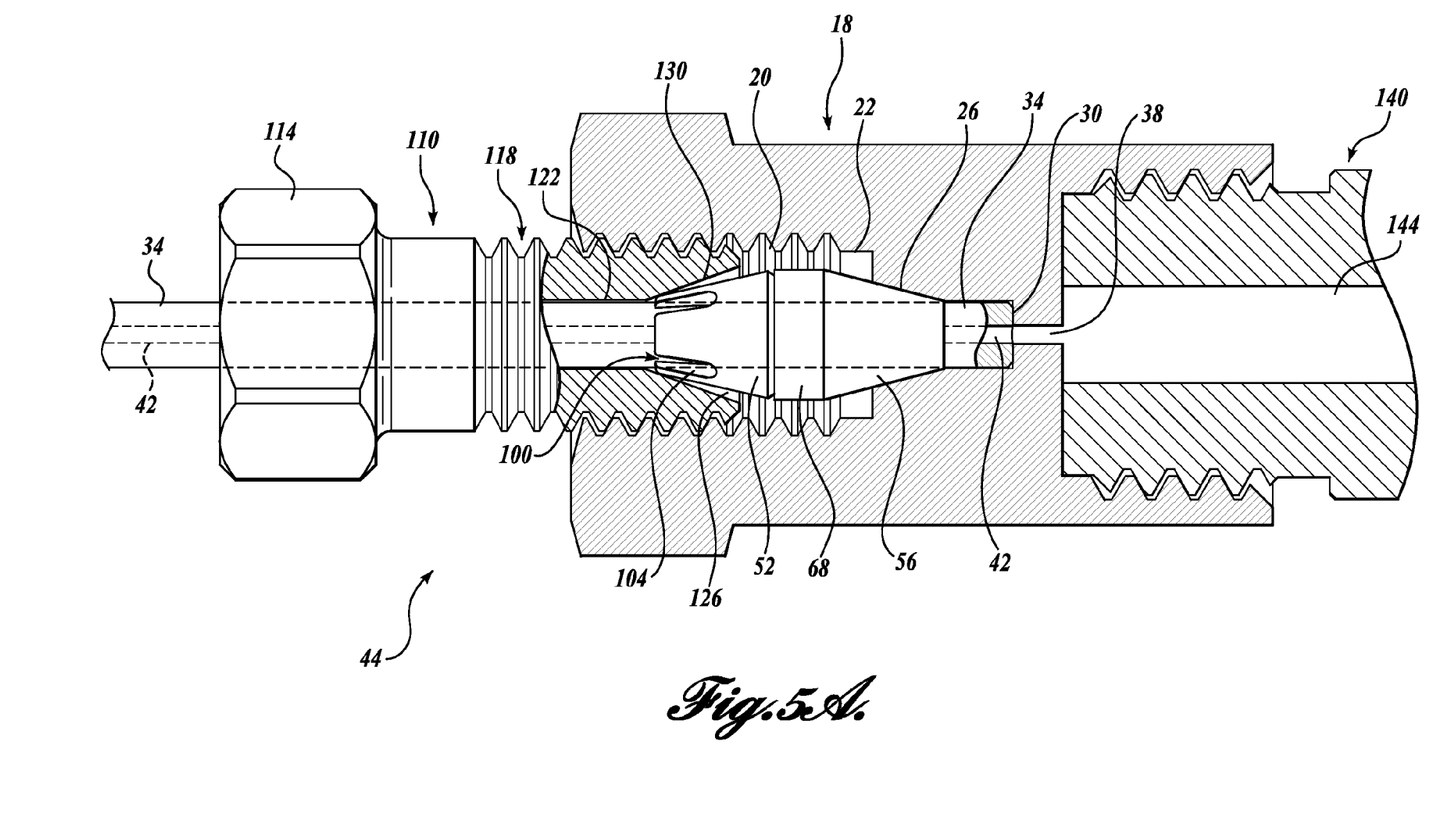
FIG. 5A is a partial cross-sectional view of a first exemplary embodiment of a fitting assembly for use in fluid transfer assemblies shown in a first position, wherein the hybrid ferrule of FIG. 2 is received within the fitting assembly.
Figure 5B:
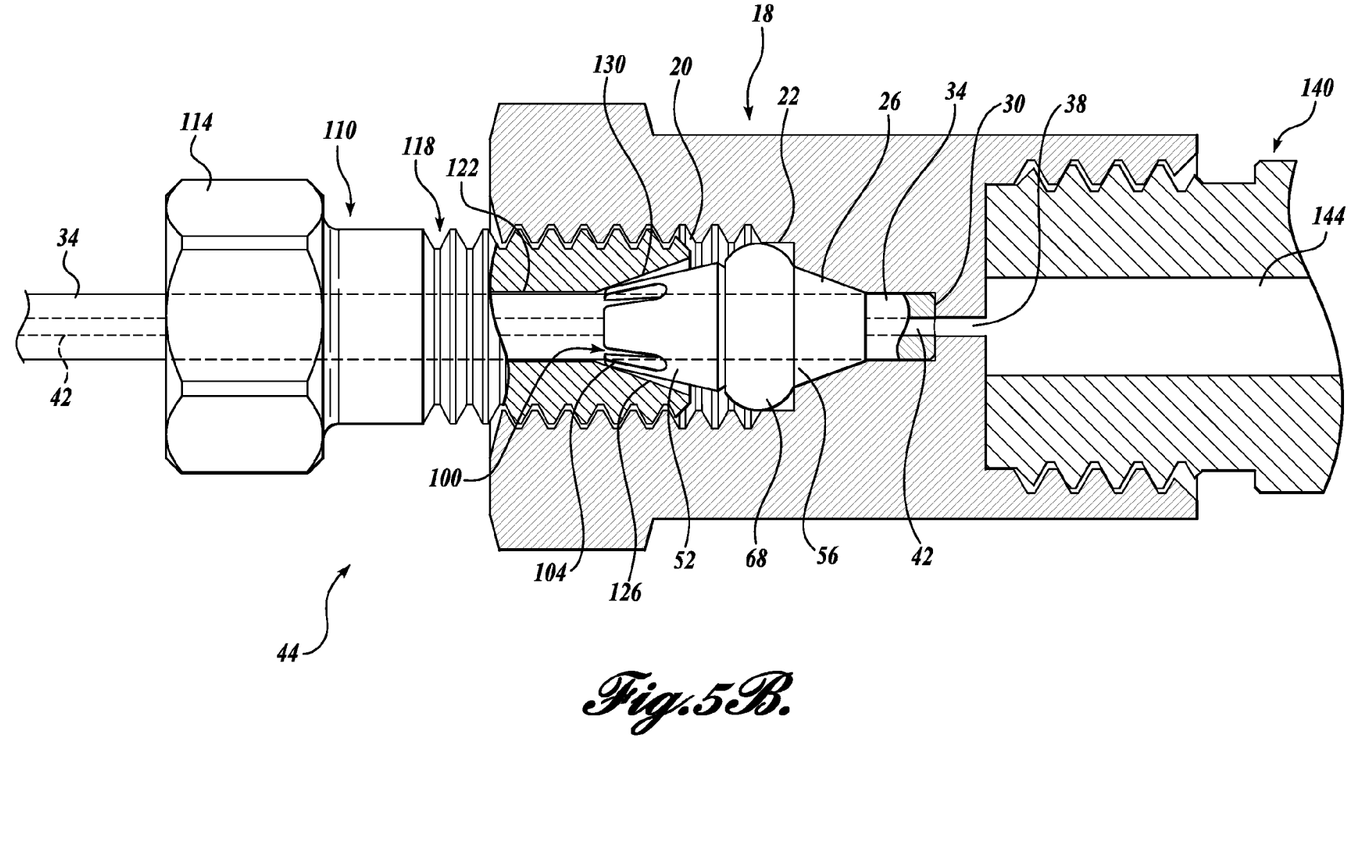
FIG. 5B is a partial cross-sectional view of the fitting assembly of FIG. 5A shown in a second position.

Preferably, the seal portion 48 defines a forty degree cone such that it is suitably adapted to be received within a variety of well-known threaded fittings similar to the fitting shown in FIGS. 1, 5A, and 5B. Such threaded fittings are readily available from a variety of well known manufacturers, such as Optimize Technologies, Inc., Swagelok Company, Parker Hannifin Corp, Valco Instruments Company Inc., Rheodyne and Upchurch Scientific (both part of the IDEX Health & Science Group), etc. For instance, the seal portion 48 may receive a 1/16th inch outer diameter tubing and fit within a standard 1/16th inch swaged fitting. It should be appreciated that the seal portion 48 may instead be larger or smaller in size to fit within various fittings for different applications.

The seal portion 48 further includes an annular collet-engaging protrusion 68 that extends axially from the end surface 66 of the seal portion 48. The annular collet-engaging protrusion 68 defines a substantially cylindrical outer surface 72 that extends from the tapered surface 56 of the of the seal portion 48. The cylindrical outer surface 72 includes a center longitudinal axis that is substantially collinear with the cylindrical passageway 64 of the hybrid ferrule 40. It should be appreciated that the outer surface 72 of the annular collet-engaging protrusion 68 may instead be curved or any other suitable contour. The annular collet-engaging protrusion 68 includes an inwardly extending lip 74 on its distal end that defines an annular receptacle or groove 76 between the lip 74 and the enlarged end surface 66 of the seal portion 48. The groove 76 is sized and configured to receive a lip 78 of a correspondingly shaped protrusion 82 of the collet portion 52.

The protrusion 82 of the collet portion 52 extends axially outwardly from a transverse end surface 92 of the collet portion 52 such that its center longitudinal axis is substantially collinear with the cylindrical passageway 64 of the hybrid ferrule 40. Moreover, the inner surface of the protrusion 82 extends from and is in substantial alignment with the surface of the second interior axial bore portion 62. In this manner, the interior surface of the cylindrical passageway 64 remains substantially smooth and of constant diameter such that the hybrid ferrule 40 may slidably receive a portion of UHPLC tubing or other suitable tubing therein. The lip 78 extends outwardly from the protrusion 82 to define an annular receptacle or groove 84 between the lip 78 and the end surface 92 of the collet portion 52. The groove 84 is sized and shaped to receive the lip 78 of the protrusion 68 extending from the seal portion 48.

As shown in FIG. 4, the collet portion 52 is secured to the seal portion 48 by mating the protrusion 82 of the collet portion 52 with the protrusion 68 of the seal portion 48. More specifically, the lip 78 of protrusion 82 is received within annular groove 76, and the lip 74 of protrusion 68 is received within annular groove 84. In this manner, the collet portion 52 and seal portion 48 are "snap fit" together to define the hybrid ferrule 40. With the collet portion 52 being made from Titanium and the seal portion 48 being made from PEEK, the collet portion 52 and seal portion 48 are preferably permanently secured together once assembled. In any event, it is preferred that the seal portion 48 be sufficiently secured to the collet portion 52 such that the hybrid ferrule 40 remains intact (the seal portion 48 remains connected to the collet portion 52) when removing the hybrid ferrule 40 from the fitting 18. Moreover, it should be appreciated that the seal portion 48 may instead be molded or otherwise formed on the collet portion 52 in any manner well known in the art.

As stated above, the collet portion 52 is of a generally frusto-conical or cone shape. Similar to the seal portion 48, the collet portion 52 includes a tapered end 86 and an enlarged end 88, wherein the enlarged end 88 defines a transverse end surface 92. An exterior, substantially smooth tapered surface 96 extends from the enlarged end 88 to the tapered end 86 such that the collet portion 52 is suitably sized and shaped to be received within a portion of a second fitting, or threaded nut 110. More specifically, and as shown in FIGS. 5A and 5B, the collet portion 52 is configured to be tightly received, or wedged within the female, cone-shaped chamber 126 of a well known externally torqued hexagonal nut 110. The nut 110 is threadably engageable with the threaded fitting 18 to compress and secure the collet potion 52 onto the tubing 34. Preferably, the collet portion 52 is configured to be received within the female, cone-shaped chamber 126 of an OPTI-LOK EXP 10-32 Hex Head Male Nut, available from Optimize Technologies, Inc., of Oregon City, Oreg. However, it should be appreciated that any other suitable nut, fitting, tightening device, or clamping device may be used to suitably compress the collet portion 52 onto the tubing 34.

The collet portion 52 further includes a plurality of axial slots 100 extending from the tapered end 86 along at least a portion of the collet portion 52 to define a plurality of axially extending fingers 104. Preferably, the collet portion 52 includes four axial slots 100 spaced equidistant from one another circumferentially about the tapered end 86 of the collet portion 52 to define four substantially identical axially extending fingers 104. However, it should be appreciated that any suitable number of axially extending fingers 104 may be used. In any event, it is preferred that a suitable number of fingers be defined and the fingers be of a suitable width and length such that they may be deformed onto the tubing 34 when engaged by the nut 110 without breaking off from the collet portion 52.

The fingers 104 deform or contract radially onto the tubing 34 when an external axial force is exerted on the fingers 104 by the female, cone-shaped chamber 126 of the nut 110. In this manner, the collet portion 52 is secured onto the tubing 34 to prevent the tubing 34 from ejecting at extreme pressures. With the collet portion 52 being made from a Titanium alloy or another suitable material, the fingers 104 spring back into their original position when the nut 110 is disengaged from the collet portion 52 such that the tubing 34 may be readjusted or removed from the ferrule 40. In addition, the collet portion 52 does not form a hard swage on the stainless steel tubing 34.

Moreover, as stated above, the seal portion 48 is made from PEEK or another suitable material such that it may seal within the fitting 18 without forming a hard swage on the tubing 34. Thus, the hardened Titanium collet portion 52 married to the softer PEEK seal portion 48 provides a hybrid ferrule 40 that seals in the female, cone-shaped chamber 28 of the fitting 18 while providing the grip necessary to prevent the stainless steel tube 34 from ejecting at high pressures. Moreover, the hybrid Titanium PEEK ferrule 40 secures onto the tubing without swaging irreversibly onto the tubing 34.

Thus, the hybrid ferrule 40 provides the necessary grip to withstand extreme pressures while providing the adjustability to be used in fittings of different sizes and tolerances. The adjustability feature is desirable, for example, when using either different female 1/16th inch pieces from the same manufacturer or when using 1/16 inch female fittings from different manufacturers. In the first case, there are slight differences with respect to the tube stop depth because of manufacturing tolerances, and the hybrid ferrule 40 needs to be repositioned on the tubing 34 to enable the tubing to bottom out in the cylindrical chamber 32 of the fitting 18. In the second instance, with different manufacturer's dimensions, the tube stop depth may differ by as much as 0.040 inches. Without the use of the hybrid ferrule 40, the tubing would either bottom out before the ferrule could engage the frusto-conical sealing surface 26 of the cone-shaped chamber 28 to make a seal, or the tubing would be off the bottom of the cylindrical chamber 32 measurably. Thus, the adjustability of the hybrid ferrule 40 enables the ferrule 40 to be reused in various fittings.

Referring to FIGS. 5A and 5B, a description of the hybrid ferrule 40 in use with a portion of the UHPLC fitting assembly 44 will be hereinafter described. The UHPLC fitting assembly 44 includes a fitting 18 as described above with respect to FIG. 1. More specifically, the threaded fitting 18 includes an internally threaded portion 20 formed near a first open end that is suitable for threadably receiving the external threads of the nut 110. The fitting 18 further includes a female, cone-shaped chamber formed at its distal, internal end that defines a frusto-conical sealing surface 26. The cone-shaped chamber is in communication with a cylindrical chamber sized to receive the end of the tubing 34 therein.

The fitting 18 further includes a passage 38 that is in communication with the cylindrical chamber and aligns with the fluid passageway 42 of the tubing 34 when the tubing is received within the cylindrical chamber. The fitting 18 may be threadably connected to a connection device 140 at a second open end of the fitting for placing the tubing 34 into communication with, for instance, a column, trap, etc., received within a cylindrical opening 144 in the connection device 140. It should be appreciated that the connection device 140 may be any suitable device used in UHPLC systems or other suitable systems.

To assemble the fitting assembly 44, the tubing 34 is inserted within the cylindrical bores of the nut 110 and the hybrid ferrule 40, and the tubing 34 is thereafter inserted into the fitting 18. The tubing 34 is moved into the fitting 18 until the tubing 34 is received within the cylindrical chamber of the female port such that the tubing is substantially bottomed out against the tube stop 30. Thereafter, the nut 110 may be tightened within the fitting to secure the hybrid ferrule 40 in its position on the tubing 34 and to define a liquid-tight seal between the tubing 34 and the fitting 18.

As described briefly above, the nut 110 is a well known externally torqued hexagonal nut that is threadably engageable with the threaded fitting 18 to compress and secure the collet potion 52 of the hybrid ferrule 40 onto the tubing 34. The nut 110 includes an enlarged end 114 that may be hex-shaped or any other suitable contour such that the nut 110 may be easily tightened within the fitting either by hand or with a suitable tool. The nut includes a threaded portion 118 extending from the enlarged end 114 and a cylindrical bore 122 extending axially along the center of the nut 110. The cylindrical bore 122 widens at the threaded end of the nut to define a frusto-conical chamber 126 having a collet-engaging surface 130.

The frusto-conical chamber 126 is sized and shaped to engage the collet portion 52 of the hybrid ferrule 40 and exert an axial force on the collet portion 52 as the nut 110 is tightened into the fitting 18. As shown in FIG. 5A, the collet-engaging surface 130 engages the fingers 104 of the collet portion 52 to compress the fingers 104 onto the tubing 34 as the nut 110 is tightened. At the same time, the collet portion 52 imparts an axial force against the seal portion 56 to drive the seal portion into sealing engagement with the frusto-conical sealing surface 26 of the fitting 18. More specifically, referring back to FIG. 4, the protrusion 82 of the collet portion 52 engages and imparts an axial force on the end surface 66 of the seal portion 48 to drive the seal portion 48 into sealing engagement against the frusto-conical sealing surface 26 of the fitting 18. As such, the seal portion 48 is sealingly engaged with the fitting 18 while the collet portion 52 is secured on the tubing 34.

When it is desired to remove the tubing 34 from the fitting 18, the nut 110 is loosened until the collet-engaging surface 130 of the nut 110 no longer substantially engages the fingers 104 of the collet portion 52. When this occurs, the fingers 104 spring back into their original state such that the tubing 34 may slide out from within the hybrid ferrule 40. Moreover, when the nut 110 and tubing 34 are removed from the fitting 18, the hybrid ferrule 40 may be removed from the fitting 18 for use in a different application or fitting. If the seal portion 56 is "stuck" within the cone-shaped portion of the fitting 18, the seal portion 48 may be pulled out of sealing engagement with the fitting 18 by pulling on the collet portion 52.

Referring to FIG. 5B, when the nut 110 is over-tightened within the fitting 18, the protrusion 82 of the collet portion 52 imparts an axial force on the end surface 66 of the seal portion 48 to further compress the seal portion 48. Because the seal portion 48 is made from PEEK or another suitable material, the over tightening causes a section of the seal portion 48 external of the cone-shaped portion of the fitting 18 to bulge outwardly into the space defined by the threaded and non-threaded portions 20 and 22 of the fitting 18. Such over tightening does not adversely affect the sealing properties of the sealing portion 48. Moreover, when it is desired to remove the tubing 34 from the fitting, the hybrid ferrule 40 can be removed from the fitting in one piece and can be re-used in its deformed state in another fitting. Thus, even when the nut 110 is fully tightened within the fitting 18, the hybrid ferrule properly seals within the fitting and secures on the tubing 34 to function in UHPLC systems.

Thus, it can be seen from the foregoing that the hybrid ferrule 40 constructed of a PEEK seal portion 48 secured to a Titanium collet portion 52 provides a ferrule that remains secured on tubing when used in extreme pressure systems while maintaining a liquid-tight seal within the fittings, wherein the ferrule may be re-used or adjusted within the fitting to accommodate various applications, fitting sizes, etc.

Figure 6:
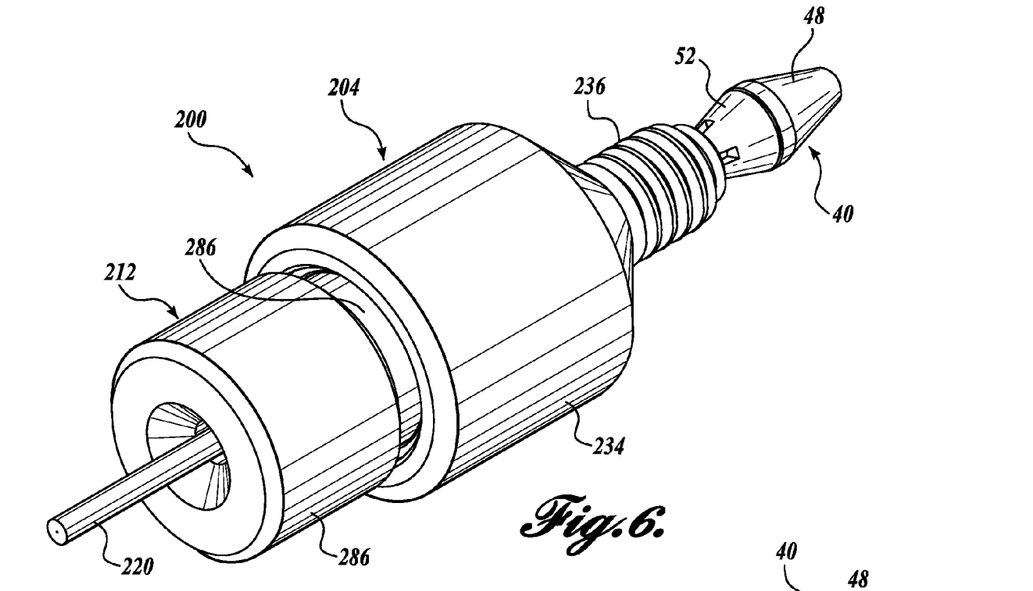
FIG. 6 is an isometric view of a second exemplary embodiment of a fitting assembly for use in fluid transfer assemblies, wherein the hybrid ferrule of FIG. 2 is received within the fitting assembly.
Figure 7:
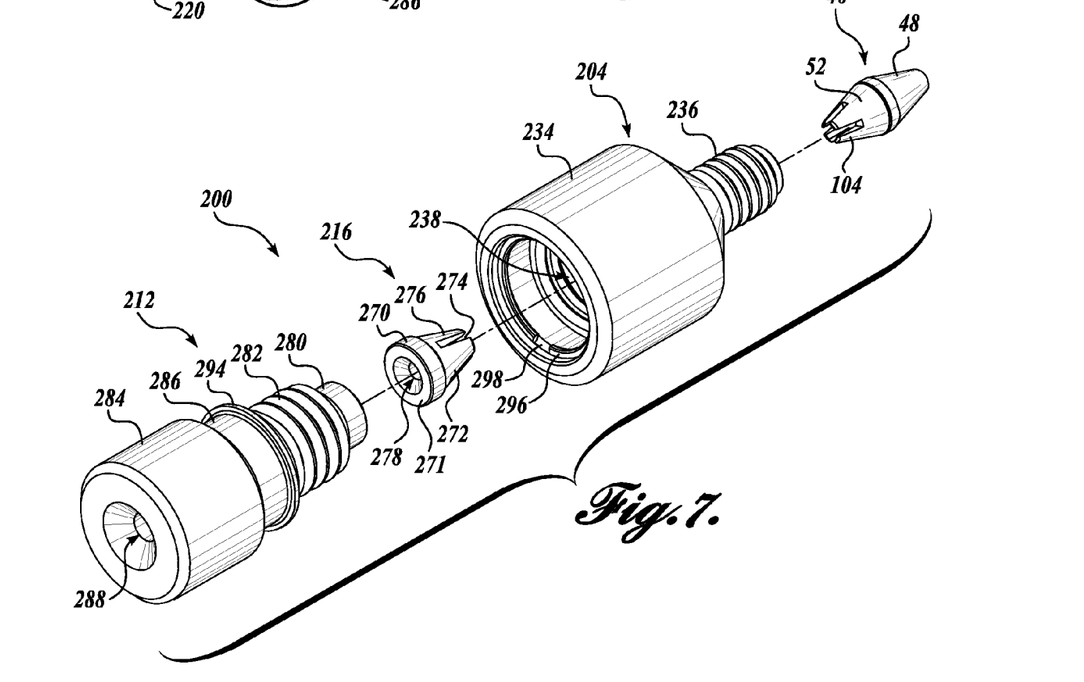
FIG. 7 is an exploded view of the fitting assembly of FIG. 6.

A second exemplary embodiment of a UHPLC fitting assembly 200 suitable for use with the hybrid ferrule 40 may best be seen by referring to FIGS. 6 and 7. Generally described, the UHPLC fitting assembly 200 is configured to suitably grip onto various types of HPLC and UHPLC fluid conduits or tubing and seal the tubing within the fitting assembly 200 without damaging or deforming the tubing. For instance, the UHPLC fitting assembly 200 is suitable for gripping and sealing onto polymer-clad fused silica tubing (e.g., PEEKsil™ tubing available from SGE Analytical Science of Austin, Tex.), polymer-sleeved fused silica tubing, or other types of tubing made from silica, borosilicate, glass silicates, etc., (hereinafter collectively referred to as "silica tubing" or a "silica conduit"), stainless steel tubing, or other suitable types of tubing used in HPLC and UHPLC systems without breaking or deforming the tube.

It should be appreciated that any suitable tubing may be used with the UHPLC fitting assembly 200. Moreover, although the UHPLC fitting assembly 200 will be described as being tightened by hand, in some embodiments the UHPLC fitting assembly 200 may be configured to be tightened with a tool, such as a wrench. It should further be appreciated that while the UHPLC fitting assembly 200 is described for use with the collet 216 and the hybrid ferrule 40, the fitting assembly 200 may instead be used with other suitable collets and ferrule assemblies. Moreover, although the fitting assembly 200 is described as a UHPLC assembly, suitable for use in fluid transfer assemblies at 30,000 PSI or higher, the fitting assembly 200 may also be adapted for use for HPLC assemblies. Thus, the descriptions and illustrations provided herein should not be seen as limiting the scope of the claimed subject matter.

Figure 8A:
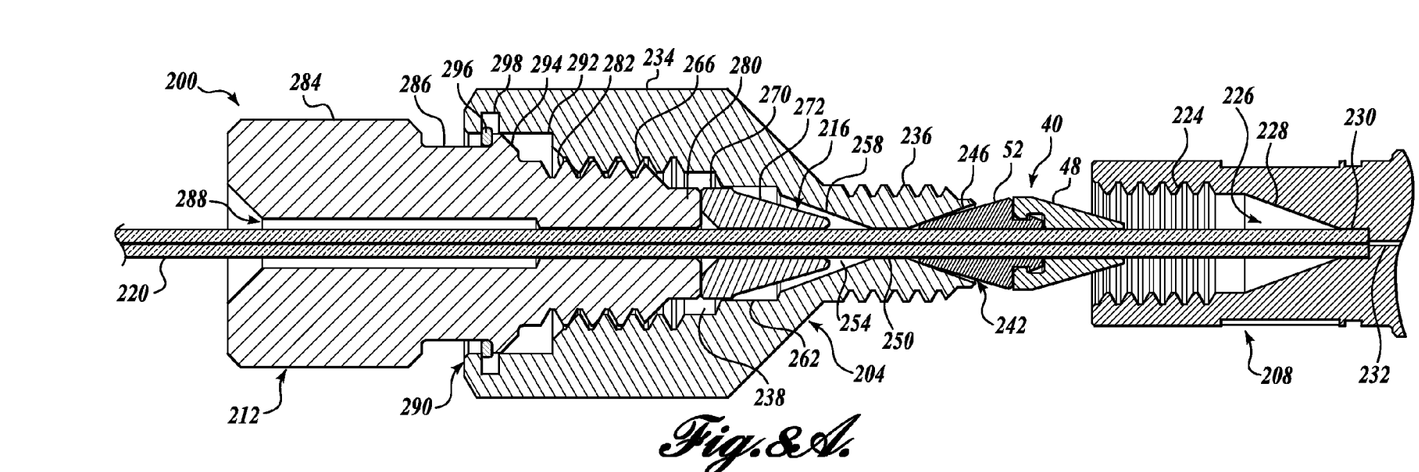
FIG. 8A is a cross-sectional view of the fitting assembly of FIG. 6 shown in a first position.

Referring to FIGS. 6, 7, and 8A, the UHPLC fitting assembly 200 will now be described in detail. The UHPLC fitting assembly 200 includes a first fitting, or a threaded housing 204 that is engageable with a second fitting, or a threaded fitting 208 (see FIG. 8A), wherein a ferrule assembly, such as the hybrid ferrule 40 is sealingly disposed between the threaded housing 204 and the threaded fitting 208. A third fitting, or a captured lock nut 212 is received within the threaded housing 204 opposite the threaded fitting 208, with a collet assembly, such as a collet 216 sealingly disposed between the lock nut 212 and the threaded housing 204.

Referring specifically to FIG. 8A, the threaded fitting 208 includes an internally threaded portion 224 formed near a first open end that is suitable for engaging external threads of the threaded housing 204. The threaded fitting 208 further includes a female, cone-shaped chamber 226 formed at its distal, internal end that defines a frusto-conical sealing surface 228. The cone-shaped chamber 226 is in communication with a cylindrical chamber 230 sized to receive the end of the tubing 220 therein. The threaded fitting 208 further includes a passage 232 that is in communication with the cylindrical chamber 230 and aligns with the fluid passageway of the tubing 220 when the tubing 220 is received within the cylindrical chamber 230. The threaded fitting 208 may be configured to place the tubing 220 into communication with, for instance, a column, trap, etc., at a second end of the threaded fitting (or through a suitable connection device).

Referring additionally to FIGS. 6 and 7, the threaded housing 204 is engageable with the threaded fitting 208 to secure the hybrid ferrule 40 therebetween in an "engaged" position. The threaded housing 204 includes an enlarged end 234 at a first end that is cylindrical in shape and includes a roughened or knurled outer surface (not depicted). In this manner, the enlarged end 234 may be used to easily tighten the threaded housing 204 by hand or with a suitable tool. It should be appreciated that the enlarged end 234 may instead be another suitable overall shape, such as hex-shaped, for tightening the threaded housing 204 by hand or with a suitable tool.

The threaded housing 204 includes an externally threaded portion 236 extending from the enlarged end 234 to define a second end of the threaded housing 204, and an axial bore 238 extending between the first and second ends. The externally threaded portion 236 is configured to be threaded into the internally threaded portion 224 of the threaded fitting 208 into the "engaged" position.

The axial bore 238 extends through the threaded housing 204 and widens at the second end to define a female, first frusto-conical chamber 242 having a collet-engaging surface 246. The first frusto-conical chamber 242 is sized and shaped to engage the collet portion 52 of the hybrid ferrule 40 and exert an axial force on the collet portion 52 as the threaded housing 204 is tightened within the threaded fitting 208 in the engaged position. By exerting an axial force on the collet portion 52, the threaded housing 204 compresses the fingers of the collet portion 52 (not labeled in FIGS. 6, 7, and 8A-8C) and secures the collet portion 52 of the hybrid ferrule 40 into releasable locking engagement on the tubing 220. At the same time, the collet portion 52 imparts an axial force against the seal portion 48 to drive the seal portion 48 into sealing engagement with the frusto-conical sealing surface 228 of the threaded fitting 208. As such, the seal portion 48 is sealingly engaged with the threaded housing 204 while the collet portion 52 is releasably secured on the tubing 220.

The threaded housing 204 is configured to exert an axial force on the hybrid ferrule 40 when it is threaded into the threaded fitting 208 in the engaged position. Similarly, the lock nut 212 is configured to impart an axial force on the collet 216 when it is threaded into the threaded housing 204 in an "engaged" position. In that regard, the threaded housing 204 includes a second frusto-conical chamber 254 disposed opposite the first frusto-conical chamber 242 that opens toward the first end of the threaded housing 204. The second frusto-conical chamber 254 is configured to sealingly receive the collet 216 therein. An axial cylindrical chamber 250 extends between the first and second frusto-conical chambers 242 and 254 to receive the tubing 220 therein.

The second frusto-conical chamber 254 transitions into a first enlarged cylindrical axial bore portion 262, which transitions into a threaded axial bore portion 266 of larger interior diameter than the first enlarged cylindrical axial bore portion 262. The threaded axial bore portion 266 defines a first open end of the threaded housing 204 at the enlarged end 234 of the threaded housing 204.

The threaded housing 204 is configured to receive a portion of the lock nut 212 within its first open end so that the lock nut 212 may impart an axial force on the collet 216. In that regard, the lock nut 212 includes an enlarged end 284 at a first end that is cylindrical in shape and includes a roughened or knurled outer surface (not depicted). In this manner, the enlarged end 284 may be used to easily tighten the lock nut 212 by hand or with a suitable tool. It should be appreciated that the enlarged end 284 may instead be another suitable overall shape, such as hex-shaped, for tightening the lock nut 212 by hand or with a suitable tool.

The lock nut 212 further includes an externally threaded portion 282 defined near the second end of the lock nut 212, and a reduced diameter portion 286 extending between the externally threaded portion 282 and the enlarged end 284. An axial bore 288 extends within the interior of the lock nut 212 between the first and second open ends for receiving the tubing 220. The externally threaded portion 282 of the lock nut 212 is configured to be threaded into the internally threaded axial bore portion 266 of the threaded housing 204 to move the lock nut 212 into the engaged position.

A cylindrically-shaped collet-engaging portion 280 extends from the externally threaded portion 282 to define the second end of the lock nut 212. The collet-engaging portion 280 is sized and configured to be received within the first enlarged cylindrical bore portion 262 of the threaded housing 204 such that the collet-engaging portion 280 may engage the collet 216. More specifically, a transverse end surface (not labeled) defined on the collet-engaging portion 280 engages a transverse end surface 271 defined on the collet 216.

The collet 216 is substantially similar to the collet portion 52 of the hybrid ferrule 40. The collet 216 is made from a Titanium alloy or another suitable material and is generally of a frusto-conical or cone shape. The collet 216 includes an annular nut-engaging portion 270 at one end and a tapered portion 272 extending therefrom, with an axial bore 278 extending between the opposite ends. The annular nut-engaging portion 270 defines a transverse end surface 271 that is engageable by the collet-engaging portion 280 of the lock nut 212.

The tapered portion 272 of the collet 216 is suitably sized and shaped to be sealingly received within the second frusto-conical chamber 254 of the threaded housing 204. More specifically, and as shown in FIG. 8C, the tapered portion 272 is configured to be tightly received, or wedged within the female, second frusto-conical chamber 254 of the threaded housing 204. The lock nut 212 engages the annular nut-engaging portion 270 to impart an axial force on the collet 216 to drive the tapered portion 272 into the second frusto-conical chamber 254, thereby sealing the collet 216 within the frusto-conical chamber 254.

At the same time, the collet 216 is compressed into releasably locking engagement on the tubing 220 to suitably grip onto the tubing 220. In that regard, the tapered portion 272 further includes a plurality of axial slots 274 extending along the tapered portion 272 that define a plurality of axially extending fingers 276. The axially extending fingers 276 are of a suitable size, shape, and number such that the fingers may deform onto the tubing 220 when engaged by the lock nut 212 without breaking off from the collet 216.

The fingers 276 deform or contract radially onto the tubing 220 when an external force is exerted on the fingers 276 by the female, second frusto-conical chamber 254 of the threaded housing 204. In this manner, the collet 216 is releasably secured onto the tubing 220 to prevent the tubing 220 from ejecting at extreme pressures. With the collet portion 220 being made from a Titanium alloy or another suitable material, the fingers 276 spring back into their original position when the lock nut 212 is disengaged from the collet 216 such that the tubing 220 may be readjusted or removed from the collet 216. In addition, the collet 216 does not form a hard swage on the tubing 220. The interior surface of the collet 216 extending along the axial bore 278 may further include texture, grooves, threading, etc., to aid in gripping onto the surface of the tubing 220.

It should be appreciated that although the collet 216 is described as being made from a Titanium alloy or another suitable material such that its fingers 276 may deform, the collet 216 may instead be made from stainless steel, glass, a polymeric material, such as PEEK, Nylon, or any other suitable materials. For instance, if the collet 216 was made from PEEK, it would form a soft swage onto the tubing 220, which would prevent damage to the tubing 220 when gripping onto the tubing 220. Moreover, the collet 216 may be made from a combination of materials, such as glass or a suitable metal (such as Titanium alloy) molded within a polymeric material. For example, metal pieces may be molded within a polymeric material so that the metal protrudes partially into the axial bore of the collet. In this manner, the metal would aid in gripping onto the tubing, while the polymeric material would form a soft swage on the tubing. Furthermore, a plurality of collets formed from glass, metal, etc. may be molded within a housing formed from a polymeric material or another suitable material to further distribute the gripping load along the tubing. Thus, it should be appreciated that the collet 216 described and illustrated herein is exemplary only, and the claimed subject should not be seen as limited in scope.

The annular nut-engaging portion 270 of the collet 216 may have substantially the same outer diameter as the inner diameter of the first enlarged cylindrical axial bore portion 262 of the threaded housing 204. In this manner, as the collet 216 is moved toward the second frusto-conical chamber 254, the tapered portion 272 of the collet 216 is aligned axially on the tubing 220. With the collet 216 in axial alignment with the tubing 220, the collet 216 may suitably grip onto the tubing 220 and seal against the collet-engaging surface 258 of the second frusto-conical chamber 254.

Likewise, the collet-engaging portion 280 of the lock nut 212 may have substantially the same outer diameter as the inner diameter of the first enlarged cylindrical axial bore portion 262. In this manner, the collet-engaging portion 280 may extend within the first enlarged cylindrical axial bore portion 262 when driving the collet 216 axially within the second frusto-conical chamber 254. Moreover, the transverse end surface of the collet-engaging portion 280 may be sized to engage substantially the entire transverse end surface 271 of the collet 216, thereby applying a substantially uniform, distributed force to the collet 216.

As noted above, the lock nut 212 is movable into an engaged position by engaging the externally threaded portion 282 of the lock nut 212 with the internally threaded axial bore portion 266 of the threaded housing 204. The fitting assembly 200 may also include a lock nut capture assembly 290 configured to retain the lock nut 212 within the interior of the threaded housing 204, when the externally threaded portion 282 of the lock nut 212 is disengaged from the internally threaded axial bore portion 266 of the threaded housing 204, or in a "disengaged" position.

The lock nut capture assembly 290 is defined by a second enlarged cylindrical axial bore portion 292 formed within the first end of the threaded housing 204. The inner diameter of the second enlarged cylindrical axial bore portion 292 is larger than the outer diameter of the reduced diameter portion 286 of the lock nut 212. In this manner, the lock nut 212 may be moved axially within the interior of the threaded housing 204 into the engaged position.

The lock nut 212 includes an annular protrusion 294 formed on the outer surface of the reduced diameter portion 286. The annular protrusion 294 is configured to engage an annular retaining clip 296 received within an annular receptacle 298 defined within the interior surface of the second enlarged cylindrical bore portion 292. In this regard, when the externally threaded portion 282 of the lock nut 212 is disengaged from the internally threaded axial bore portion 266 of the threaded housing 204 (i.e., in a disengaged position), the annular retaining clip 296 will retain or capture the lock nut 212 within the threaded housing 204.

It should be appreciated that any other suitable lock nut capture assembly 290 may instead be used to capture the lock nut 212 within the threaded housing 204. Moreover, it should be appreciated that in some embodiments, the lock nut capture assembly 290 may not be used such that the lock nut 212 is removable from the threaded housing 204 in the disengaged position.

Figure 8B:
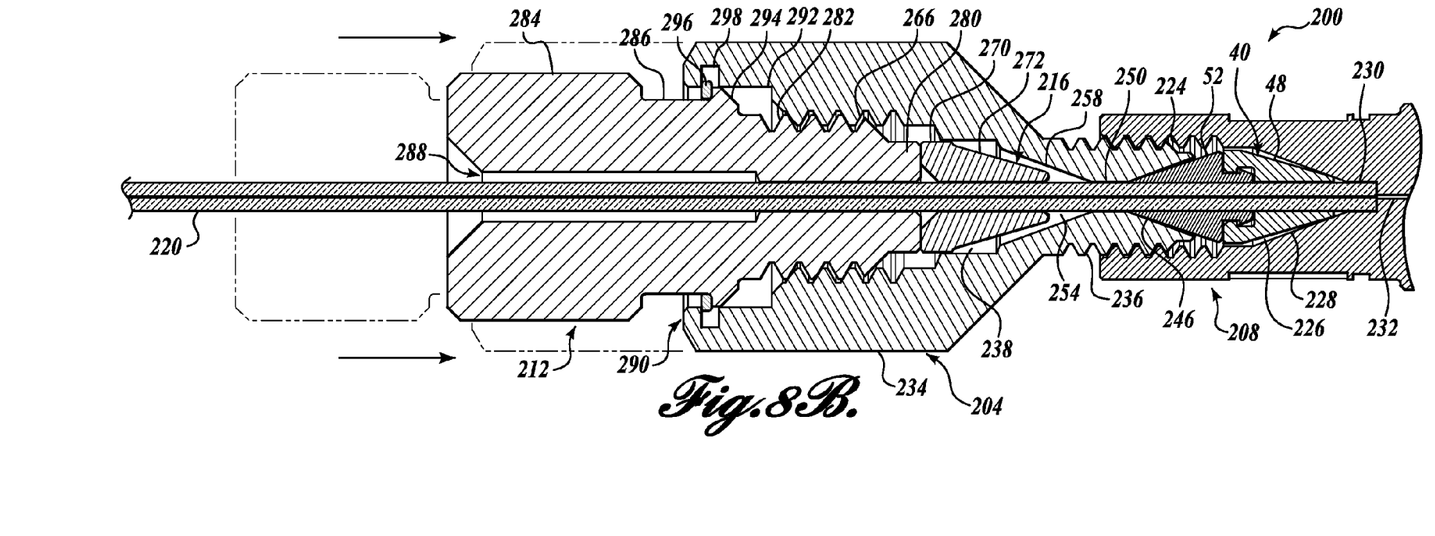
FIG. 8B is a cross-sectional view of the fitting assembly of FIG. 6 shown in a second position.
Figure 8C:
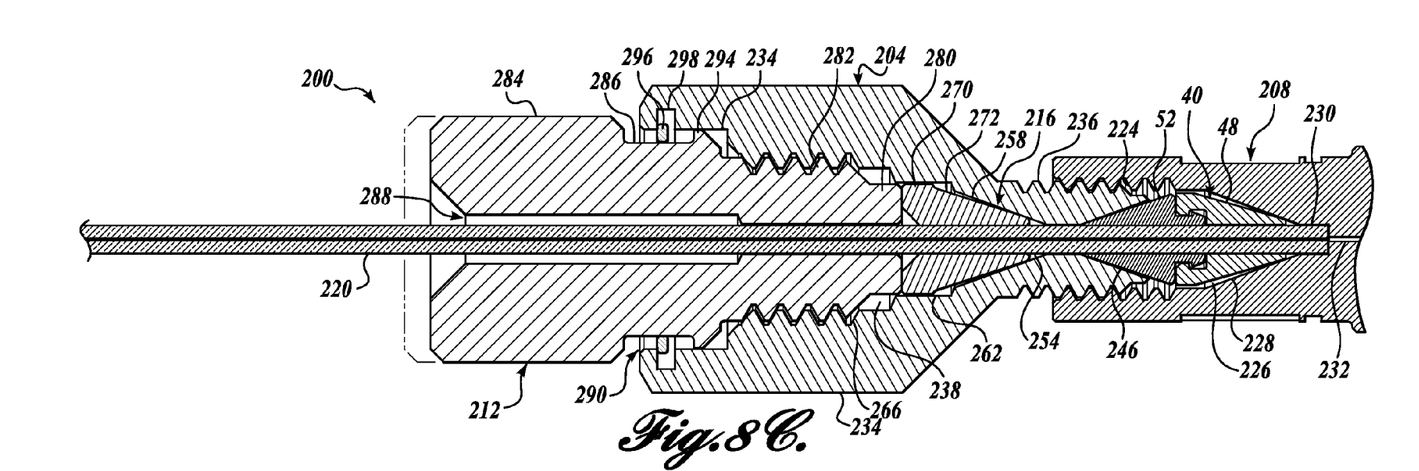
FIG. 8C is a cross-sectional view of the fitting assembly of FIG. 6 shown in a third position.

Referring to FIGS. 8A-8C, the operation of the fitting assembly 200 will now be described in detail. Referring first to FIG. 8A, the fitting assembly 200 is shown with threaded housing 204 disengaged from the threaded fitting 208, and with the lock nut 212 disengaged from the threaded housing 204. Tubing 220 extends through the longitudinal axial bore of the fitting assembly 200 (defined by the axial bores of the lock nut 212, the collet 216, the threaded housing 204, and the hybrid ferrule 40) and protrudes from the hybrid ferrule 40. The tubing 220 is moved into the threaded fitting 208 until the tubing 220 is substantially bottomed out within the cylindrical chamber 230, as shown in FIG. 8A.

Referring to FIG. 8B, with the collet portion 52 of the hybrid ferrule 40 positioned within the first frusto-conical chamber 242 of the threaded housing 204, the threaded housing 204 is tightened within the threaded fitting 208 to move the threaded housing 204 into the engaged position. Tightening the threaded housing 204 within the threaded fitting 208 secures the hybrid ferrule 40 in its position on the tubing 220 and defines a liquid-tight seal between the tubing 220 and the threaded fitting 208.

More specifically, by tightening the threaded housing 204 within the threaded fitting 208 (i.e., in the engaged position), the threaded housing 204 imposes an axial force on the collet portion 52 of the hybrid ferrule 40 through the collet-engaging surface 246. The collet portion 52 drives the PEEK seal portion 48 into sealing engagement with the frusto-conical sealing surface 228 of the threaded fitting 208. At the same time, the collet-engaging surface 246 compresses the fingers of the collet portion 52 onto the tubing 220 to securely position the hybrid ferrule 40 on the tubing 220.

The threaded housing 204 may be hand-tightened within the threaded fitting 208 rather than using a tool, such as a wrench. If a tool was use to over-tighten the threaded housing 204 within the threaded fitting 208, the PEEK seal portion 48 of the hybrid ferrule 40 can deform, as described above with respect to FIG. 5B. Deformation of the seal portion 48 can cause the tubing 220 to be driven further into the cylindrical chamber 230, which can cause the tubing to fracture. Thus, when the tubing is made of more delicate materials (such as silica), hand tightening is preferred. However, it should be appreciated that a tool may be used to tighten the threaded housing 204 within the threaded fitting 208 with the same amount of force used for hand-tightening.

With the threaded housing 204 hand-tightened within the threaded fitting 208 in the engaged position to secure the hybrid ferrule 40 onto the tubing 220, the hybrid ferrule 40 can withstand fluid pressures of up to about 15,000 psi. To increase the fluid pressure capabilities of the fitting assembly 200, the lock nut 212 is moved into the engaged position, or it is tightened within the threaded housing 204 to secure the collet 216 onto the tubing 220 and to seal the collet 216 within the threaded housing 204.

Referring to FIG. 8C, the lock nut 212 is tightened within the threaded housing 204 by gripping and turning the enlarged portion 284 of the lock nut 212. In certain embodiments, the threading is configured such that only about one quarter (¼) of a turn is needed to fully tighten the lock nut 212 within the threaded housing 204 (i.e., moved into the engaged position).

When moved into the engaged position, the collet-engaging portion 280 of the lock nut 212 imparts an axial force onto the annular nut-engaging portion 270 of the collet 216. The collet 216 is driven into engagement with the collet-engaging surface 258 of the second frusto-conical chamber 254 to seal the collet 216 within the second frusto-conical chamber 254. At the same time, the collet-engaging surface 258 compresses the fingers 276 of the collet 216 onto the tubing 220 to securely position the collet 216 on the tubing 220.

When the collet 216 is compressed onto the tubing 220, the collet 216 grips onto the tubing 220 without driving the tubing 220 further towards the hybrid ferrule 40 (and therefore, further within the cylindrical chamber 230). Moreover, as noted above, with the threaded housing 204 tightened within the threaded fitting 208 in the engaged position, the tubing 220 is securely positioned within the hybrid ferrule 40. As such, the tubing 220 is not driven further into the cylindrical chamber 230, preventing any fracturing of the end of the tubing 220.

In that regard, the threaded housing 204 may be either hand-tightened within the threaded fitting 208 or may instead be tightened with a tool. Hand-tightening the threaded housing 204 within the threaded fitting 208 will sufficiently compress the collet 216 onto the tubing 220. However, because there is no danger of driving the tubing 220 further into the cylindrical chamber 230 (with the possibility of fracturing the tubing 220), a tool may instead be used.

The gripping force of the collet 216 in addition to the hybrid ferrule 40 enables the fitting assembly 200 to withstand fluid pressures up to about 30,000 psi and higher. Moreover, the gripping load is distributed over two areas of the tubing 220, rather than point loading at only a single ferrule assembly, which can cause damage to the tubing. It should be appreciated that the fitting assembly 200 may be modified to include additional collet and ferrule assemblies for gripping onto the tubing 220. In this manner, the gripping load may be distributed over three or more areas of the tubing 220. By distributing the load over three or more areas of the tubing, the fitting assembly 200 may be able to withstand fluid pressures much greater than 30,000 psi. Thus, it should be appreciated that the fitting assembly 200 may be adapted or modified to include less or more areas of distributed load for the intended application.

To remove or otherwise reposition the tubing 220 within the fitting assembly 200, the lock nut 212 is loosened by hand (or with a tool, depending on how originally tightened) to loosen the grip of the collet 216 on the tubing 220 and move the lock nut 212 into the disengaged position. With the lock nut 212 in the disengaged position, the fingers 276 of the collet 216 may spring back to their original, undeformed state (see FIG. 8B).

Similarly, the threaded housing 204 is loosened by hand to loosen the grip of the hybrid ferrule 40 on the tube 220 and move the threaded housing 204 into the disengaged position. The threaded housing 204 may be removed from within the threaded fitting 208, thereby allowing the fingers of the collet portion 52 of the hybrid ferrule 40 to spring back to their original, undeformed state (see FIG. 8A). With the collet 216 and hybrid ferrule 40 loosely disposed on the tubing 220, the position of the fitting 200 may be readjusted on the tubing 220, or a new fitting may be used with the same tubing 220.

Figure 9:
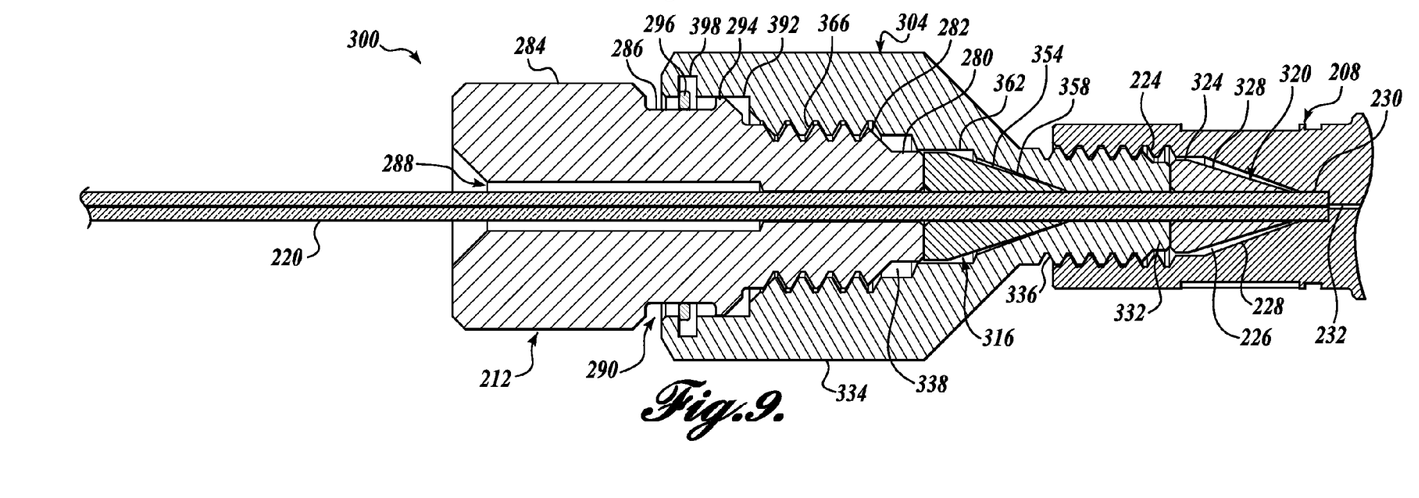
FIG. 9 is a cross-sectional view of a third exemplary embodiment of a fitting assembly for use in fluid transfer assemblies.

Referring to FIG. 9, a third exemplary embodiment of a UHPLC fitting assembly 300 will now be described. The fitting assembly 300 is configured to suitably grip onto various types of HPLC and UHPLC tubing and seal the tubing within the fitting assembly 300 without damaging or deforming the tubing. For instance, the UHPLC fitting assembly 300 is suitable for gripping and sealing onto stainless steel tubing, silica tubing, or other suitable types of tubing used in HPLC and UHPLC systems without breaking or deforming the tubing.

The fitting assembly 300 is substantially similar to the fitting assembly 200 described above except for the differences hereinafter provided. In that regard, reference numerals used to describe and illustrate components of the fitting assembly 200 have been used for description and illustration of the fitting assembly 300 where the components are substantially identical.

The fitting assembly 300 differs from fitting assembly 200 described above in that the hybrid ferrule 40 is not disposed within the threaded fitting 208. Rather, a ferrule 320 is received within the threaded fitting 208 for engaging and sealing against the frusto-conical sealing surface 228 of the cone-shaped chamber 226. The ferrule 320 includes an annular fitting-engaging portion 324 at a first end of the ferrule 320 that defines a transverse end surface (not labeled). The transverse end surface of the fitting-engaging portion 324 is engageable by a portion of the threaded housing 304 to drive the ferrule 320 into the threaded fitting 208 when the threaded housing 304 is in an engaged position. A tapered portion 328 extends from the fitting-engaging portion 324 that is engageable with the frusto-conical sealing surface 228. The ferrule 320 may be comprised of a polymeric material, such as PEEK, to seal against the frusto-conical sealing surface 228. Moreover, the polymeric ferrule 320 forms a soft swage as it grips onto the tubing 220, thereby preventing any damage to the tubing 220.

The threaded housing 304 is substantially similar to threaded housing 204 described above. In that regard, the threaded housing 304 is configured to receive a collet 316 in a second frusto-conical chamber 354, wherein the collet 316 is substantially similar to collet 216 described above. In that regard, when the collet 316 is driven into the second frusto-conical chamber 354 and compressed onto the tubing 220, the collet 316 grips onto the tubing 220 without driving the tubing 220 further towards the ferrule 320 (and therefore, further within the cylindrical chamber 230). As such, the tubing 220 is not driven further into the cylindrical chamber 230, preventing any fracturing of the end of the tubing 220.

However, the threaded housing 304 does not include a first frusto-conical chamber at its second end. Rather, the second end is defined by a ferrule-engaging portion 332 that is configured to engage and impart an axial force on the ferrule 320. The ferrule-engaging portion 332 defines a transverse end surface (not labeled) that is engageable with the transverse end surface of the fitting-engaging portion 324 of the ferrule 320.

The gripping force of the collet 316 in addition to the ferrule 320 enables the fitting assembly 200 to withstand higher fluid pressures than if the ferrule 320 was used alone. Moreover, the gripping load is distributed over two areas of the tubing 220, rather than point loading at only a single ferrule assembly, which can cause damage to the tubing 220.

To remove or otherwise reposition the tubing 220 within the fitting assembly 300, the lock nut 212 is loosened by hand (or with a tool, depending on how originally tightened) to loosen the grip of the collet 316 on the tubing 220. The lock nut 212 is loosened until it moves into the disengaged position, thereby allowing the fingers of the collet 316 to spring back to their original, undeformed state.

Similarly, the threaded housing 304 is loosened by hand to loosen the grip of the ferrule 320 on the tubing 220. The threaded housing 304 may be removed from within the threaded fitting 208, thereby allowing the polymeric ferrule 320 to be removed from within the threaded fitting 208 and the tubing 220. With the collet 316 and ferrule 320 loosely disposed on the tubing 220, the position of the fitting 300 may be readjusted on the tubing 220, or a new fitting may be used with the same tubing 220.

While the preferred embodiment of the invention has been illustrated and described, it will be appreciated that various changes can be made therein without departing from the spirit and scope of the present disclosure. For instance, it should be appreciated that although the fitting assemblies 200 and 300 are shown in use with certain collet and ferrule assemblies, the fitting assemblies 200 and 300 may instead be used with any suitable collet and ferrule assemblies. Moreover, aspects of the various fitting assemblies described above may be used in combination with other fitting assemblies or may instead be used in isolation.

The embodiments of the invention in which an exclusive property or privilege is claimed are defined as follows:

1. A fitting assembly for use in a fluid transfer assembly having a fluid conduit, the fitting assembly comprising:
   (a) a first fitting having first and second ends and a bore extending between the first and second ends for receiving the fluid conduit, wherein the first end sealingly disposes a ferrule assembly within a second fitting in an engaged position, wherein the first end of the first fitting biases the ferrule assembly into releasable locking engagement with the fluid conduit in the engaged position, and wherein the ferrule assembly comprises:
       (i) a frusto-conical seal portion having a tapered end, an enlarged end, and a first bore sized and configured to receive the fluid conduit, the seal portion formed from a first material; and
       (ii) a frusto-conical collet portion having a tapered end and an enlarged end, the enlarged end of the collet portion mated with the enlarged end of the seal portion, the collet portion having a second bore in substantial alignment with the first bore, the collet portion including at least one axial finger extending along the tapered end of the collet portion that is configured to be biased into locking engagement with the fluid conduit, wherein the collet portion is formed from a second material; and
   (b) a third fitting having first and second ends and a bore extending between the first and second ends for receiving the fluid conduit, wherein the first end sealingly disposes a collet assembly within the first fitting in the engaged position.

2. The fitting assembly of claim 1, wherein the ferrule assembly comprises a ferrule having a bore for receiving the fluid conduit, a tapered end, and an enlarged end, and wherein the ferrule is made from a polymeric material.

3. The fitting assembly of claim 1, wherein the first end of the third fitting is configured to bias the collet assembly into releasable locking engagement with the fluid conduit in the engaged position.

4. The fitting assembly of claim 2, wherein the collet assembly comprises a collet having a bore for receiving the fluid conduit, the collet having a tapered end, an enlarged end, and at least one axial finger extending along the tapered end that is configured to be biased into locking engagement with the fluid conduit, the enlarged end engageable by the first end of the third fitting.

5. The fitting assembly of claim 4, wherein the collet is formed from a material chosen from the group consisting of a titanium alloy, stainless steel, a polymer, or a combination thereof.

6. The fitting assembly of claim 1, wherein the third fitting is moveable into a disengaged position to move the collet assembly out of sealing engagement with the first fitting.

7. The fitting assembly of claim 6, further comprising a capture assembly configured to retain the third fitting within a portion of the first fitting in the disengaged position.

8. The fitting assembly of claim 1, wherein the fluid conduit is a silica conduit.

9. A fitting assembly for use in a fluid transfer assembly having a fluid conduit, the fitting assembly comprising:
(a) a first fitting having first and second ends and a bore extending between the first and second ends for receiving the fluid conduit, wherein the first end sealingly disposes a ferrule assembly within a second fitting in an engaged position, the ferrule assembly made at least in part from a first material suitable for sealing within the second fitting, wherein the first end of the first fitting biases the ferrule assembly into releasable locking engagement with the fluid conduit in the engaged position, wherein the ferrule assembly comprises:
(i) a frusto-conical seal portion having a tapered end, an enlarged end, and a first bore sized and configured to receive the fluid conduit, the seal portion formed from the first material; and
(ii) a frusto-conical collet portion having a tapered end and an enlarged end, the enlarged end of the collet portion mated with the enlarged end of the seal portion, the collet portion having a second bore in substantial alignment with the first bore, the collet portion including at least one axial finger extending along the tapered end of the collet portion that is configured to be biased into locking engagement with the fluid conduit, wherein the collet portion is formed from a second material; and
(b) a third fitting having first and second ends and a bore extending between the first and second ends for receiving the fluid conduit, wherein the first end sealingly disposes a collet assembly within the first fitting in an engaged position, wherein the collet assembly comprises a collet made from the second material that is harder than the first material and of a suitable configuration to releasably grip onto the fluid conduit in the engaged position, the collet having a bore for receiving the fluid conduit, the collet having a tapered end, an enlarged end, and at least one axial finger extending along the tapered end that is biased into locking engagement with the fluid conduit, the enlarged end engageable by the first end of the third fitting.

10. The fitting assembly of claim 9, wherein the ferrule assembly comprises a ferrule having a bore for receiving the fluid conduit, a tapered end, and an enlarged end, and wherein the ferrule is made from a polymeric material.

11. The fitting assembly of claim 9, further comprising a capture assembly configured to retain the third fitting within a portion of the first fitting in a disengaged position.

12. A fitting assembly for use in a fluid transfer assembly having a fluid conduit, the fitting assembly comprising:
(a) a first fitting comprising:
(i) first and second ends;
(ii) a first internal opening defined at the first end of the first fitting; and
(iii) a first internal frusto-conical chamber that opens towards the second end of the first fitting, the first internal frusto-conical chamber in communication with the first internal opening;
(b) a second fitting comprising:
(i) first and second ends;
(ii) a second internal opening defined at the first end of the second fitting for receiving the second end of the first fitting in an engaged position;
(iii) an internal cylindrical chamber defined near the second end of the second fitting that is sized and configured to receive an end of the fluid conduit; and
(iv) an internal second frusto-conical chamber that opens towards the second end of the second fitting, the internal second frusto-conical chamber positioned axially between the second internal opening and the cylindrical chamber such that the cylindrical chamber is nearest the second end of the second fitting, the second internal opening is nearest the first end of the second fitting, and the internal second frusto-conical chamber is positioned between the internal cylindrical chamber and the second internal opening, wherein the internal second frusto-conical chamber is in communication with the internal cylindrical chamber and the second internal opening;
(c) a third fitting having first and second ends, wherein the first end of the third fitting is receivable within the first internal opening of the first fitting in the engaged position;
(d) a ferrule assembly disposed between the first and second fittings, at least a portion of the ferrule assembly made from a first material suitable for sealing within the internal second frusto-conical chamber, wherein the second end of the first fitting engages and sealingly disposes the ferrule assembly within the internal second frusto-conical chamber of the second fitting in the engaged position, and wherein the second end of the first fitting biases the ferrule assembly into releasable locking engagement directly with an exterior surface of the fluid conduit in the engaged position, wherein the ferrule assembly comprises:
(i) a frusto-conical seal portion having a tapered end, an enlarged end, and a first bore sized and configured to receive the fluid conduit, the seal portion formed from the first material; and
(ii) a frusto-conical collet portion having a tapered end and an enlarged end, the enlarged end of the collet portion mated with the enlarged end of the seal portion, the collet portion having a second bore in substantial alignment with the first bore, the collet portion including at least one axial finger extending along the tapered end that is configured to be biased into locking engagement with the fluid conduit, wherein the collet portion is formed from a second material; and
(e) a collet assembly having a collet disposed between the first and third fittings, wherein the second end of the third fitting engages the collet within the first fitting in the engaged position, and wherein the collet is made from the second material that is harder than the first material and of a suitable configuration to releasably grip onto the fluid conduit in the engaged position, wherein the collet has a tapered end and an enlarged end, the enlarged end engageable by the second end of the third fitting.

13. The fitting assembly of claim 12, wherein the collet includes at least one axial finger extending along the tapered end that is configured to be biased into releasable locking engagement with the fluid conduit.

14. The fitting assembly of claim 12, wherein the enlarged end of the frusto-conical seal portion is engageable by the second end of the first fitting.

15. The fitting assembly of claim 12, wherein the ferrule assembly comprises a ferrule having a bore for receiving the fluid conduit, a tapered end, and an enlarged end, and wherein the ferrule is made from a polymeric material.

16. The fitting assembly of claim 12, further comprising a capture assembly configured to retain the third fitting within a portion of the first fitting in a disengaged position.

\* \* \* \* \*